Figure 1:
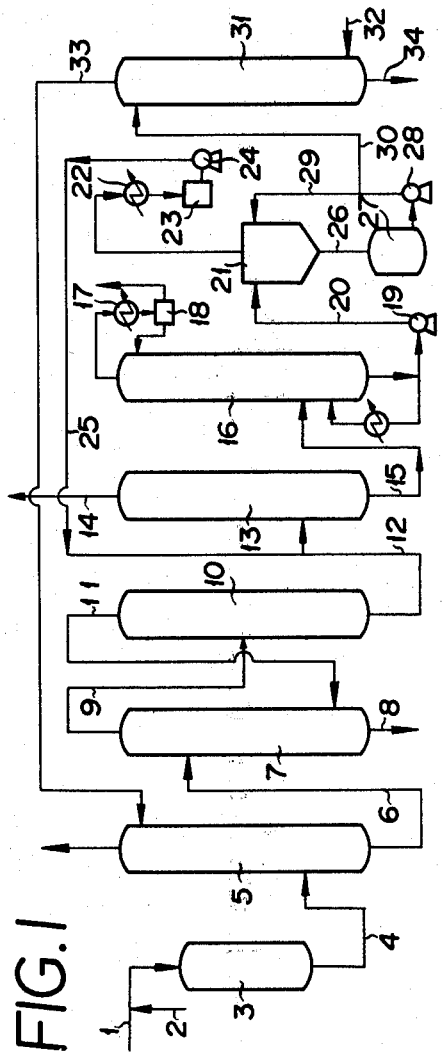

United States Patent [19]

Sato et al.

[11] 4,317,926

[45] Mar. 2, 1982

[54] PROCESS FOR PREPARING AND RECOVERING ACRYLIC ACID

[75] Inventors: Takahisa Sato; Masao Baba; Michito Okane, all of Himeji, Japan

[73] Assignee: Nippon Shokubai Kagaku Kogyo Co., Ltd., Osaka, Japan

[21] Appl. No.: 3,405

[22] Filed: Jan. 15, 1979

[30] Foreign Application Priority Data

Jan. 19, 1978 [JP] Japan .................................... 53-3753
Jan. 20, 1978 [JP] Japan .................................... 53-4346

[51] Int. Cl.$^3$ ...................... C07C 51/25; C07C 51/50; C07C 57/05; C07C 57/055
[52] U.S. Cl. .................................... 562/532; 203/8; 203/28; 203/60; 203/72; 203/73; 203/DIG. 21; 560/185; 560/208; 560/218; 562/536; 562/545; 562/548; 562/598; 562/599; 562/600; 562/608; 568/753
[58] Field of Search ................ 562/599, 600, 545–547, 562/532, 548, 608, 534–536; 560/208, 218; 203/8, 28, DIG. 21, 60, 73, 72; 568/753

[56] References Cited

U.S. PATENT DOCUMENTS

| 2,941,007 | 6/1960 | Callahan | 562/535 |
| 3,926,744 | 12/1975 | Noll et al. | 562/535 |
| 4,124,634 | 11/1978 | Gotoh et al. | 562/535 |

FOREIGN PATENT DOCUMENTS

| 1238962 | 7/1971 | United Kingdom . |
| 1427223 | 3/1976 | United Kingdom . |
| 1436535 | 5/1976 | United Kingdom . |

*Primary Examiner*—Vivian Garner
*Attorney, Agent, or Firm*—Omri M. Behr

[57] ABSTRACT

In a process for producing acrylic acid which comprises contacting with water an acrylic acid-containing reaction product gas which has been obtained by the catalytic vapor phase oxidation of an olefinic compound of a general formula, $CH_2=CHX$, wherein X represents at least one group selected from the group consisting of $CH_3$ and CHO, with a molecular oxygen-containing gas thereby collecting the acrylic acid in the form of an aqueous solution, separating the acrylic acid from the aqueous solution, and refining the thus separated acrylic acid, the improvement comprising a step of subjecting the bottom liquor of a rectification tower for acrylic acid to a decomposition evaporation and a step of subjecting the evaporation residue having a composition of 1–25 wt % of acrylic acid, 9–49 wt % of acrylic acid dimer, wherein total amount of the acrylic acid and its dimer is in the range of 10–50 wt %, and correspondingly 90–50 wt % of other matters to an extraction with water to separate the acrylic acid, its dimer and hydroquinone by the extraction.

10 Claims, 2 Drawing Figures

PROCESS FOR PREPARING AND RECOVERING ACRYLIC ACID

This invention generally relates to a process for recovering acrylic acid and particularly, to a process for recovering acrylic acid from an acrylic acid dimer or trimer produced in the production process of acrylic acid, simultaneously with hydroquinone which is employed as a polymerization inhibitor in the production process. More specifically, the invention is concerned with a process for recovering acrylic acid together with hydroquinone in which acrylic acid oligomers which are by-produced in an apparatus of producing acrylic acid by the catalytic vapor phase oxidation reaction of propylene or acrolein and concentrated in a bottom liquor of a final step rectification tower for acrylic acid are thermally decomposed to efficiently recover them as acrylic acid, together with hydroquinone which is used as a polymerization inhibitor in the rectifying step and concentrated in the bottom liquor of the acrylic acid rectifier.

As is well known, a process of producing acrylic acid by the catalytic vapor phase oxidation of propylene or acrolein with a molecular oxygen-containing gas comprises a number of steps including an oxidation step, a step of collecting the oxidation reaction product by absorption with water to give an aqueous solution thereof, a step of removing water from the aqueous solution by extraction of acrylic acid with an extraction solvent such as ethyl acetate, ethyl acrylate or the like, a solvent separation step, a step of separating the by-produced acetic acid, and an acrylic acid refining step.

It is well known that acrylic acid polymerizes so readily that, in the above-mentioned steps, its polymer tends to be formed in the apparatus, particularly in the respective distillation towers, frequently impeding the operations of the apparatus and thus leading to a lowering of yield of acrylic acid to be a product. To avoid this, there has been widely accepted heretofore, as a method of inhibiting the polymerization of acrylic acid, a method of adding polymerization inhibitors to the steps, particularly to the absorption and distillation towers. As a typical polymerization inhibitor there is well known hydroquinone, which is generally used in combination with other effective polymerization inhibitor such as molecular oxygen, phenols, e.g., phenol, cresol and tert-butyl catechol, amines, e.g., diphenylamine, phenothiazine and methylene blue, quinones, e.g., hydroquinone monomethylether, or inorganic and organic salts, e.g., copper dimethyldithiocarbamate, copper diethyldithiocarbamate, copper dibutyldithiocarbamate and copper salycilate.

Acrylic acid readily undergoes not only a polymerization as mentioned above, but also oligomerizations such as a dimerization and a trimerization. Such oligomerization is considered to result mainly from consecutive reactions. In the aforementioned steps, a dimer is chiefly produced.

Further, formation of the acrylic acid dimer by the dimerization of acrylic acid is considerably influenced by the temperature and residence time and is almost impossible to be completely suppressed by the addition of the above-indicated polymerization inhibitors. That is to say, the formation of the acrylic acid dimer depends on the temperature and residence time. Accordingly, it is believed that even though the heating temperature is decreased or the residence time is shortened in the usual acrylic acid-rectifying step and particularly in the distillation step, 1–5 wt % of the acrylic acid dimer is inevitably formed. The thus formed dimer of acrylic acid and the added polymerization inhibitors are successively concentrated in the respective steps and concentrated in the bottom of the final step rectification tower to levels of 10–50 times as high as the initial concentrations, respectively.

To discharge, as it is, the bottom liquor containing the dimer of acrylic acid and polymerization inhibitors at such high concentrations is very disadvantageous from an economical standpoint. Accordingly, there have been proposed several processes of utilizing the bottom liquor, particularly processes of decomposing the acrylic acid dimer into acrylic acid for recovery. For instance, Japanese Patent Publication No. 45-19281 discloses a process of decomposing polymeric materials to recover as acrylic acid monomer by thermal treating of a bottom residue in the presence of a catalyst such as of a secondary amine, a tertiary amine or a tertiary phosphine. Further, there is disclosed, in U.S. Pat. No. 3,086,046, a process of recovering acrylic acid by evaporating a bottom residue of a distillation tower in a thin layer evaporator and passing the resulting acrylic acid dimer-containing vapor into a heated stainless steel tube to subject the dimer to the decomposition reaction. However, these processes are not satisfactory in view of a fact that the maximum recovery of acrylic acid is as low as 60–80 wt % even if the processes are conducted on a laboratory scale and will be practically lowered since a highly viscous residue is formed in large amount.

Still further, in Japanese Laid-open Patent Publication No. 51-91,208, there is proposed a process in which the bottom liquor of a rectification tower is evaporated in an evaporator to a level of 60–80% and the polymerization inhibitor contained in the resulting distillate is reused in the rectifying step. However, this process does not produce a satisfactory effect on the recovery of polymerization inhibitor. This is because the residue discharged from the evaporator still contains not only hydroquinone but also substantial amounts of other polymerization inhibitors and a dimer or trimer of acrylic acid, and these components have to be eventually discharged.

Accordingly, it is an object of the present invention to provide a process for recovering acrylic acid from oligomers of acrylic acid formed during the production of acrylic acid.

It is another object of the present invention to provide a process for recovering both acrylic acid from the acrylic acid dimer concentrated in the bottom liquor of a rectification tower for acrylic acid, and hydroquinone.

The above objects can be achieved by a recovery process for acrylic acid in a process for producing acrylic acid which comprises contacting, with water, an acrylic acid-containing reaction product gas which has been obtained by the catalytic vapor phase oxidation of an olefinic compound of a general formula, $CH_2=CHX$, wherein X is at least one group selected from the group consisting of $CH_3$ and CHO with a molecular oxygen-containing gas thereby collecting the acrylic acid in the form of an aqueous solution, separating the acrylic acid from the aqueous solution, and refining the thus separated acrylic acid, the recovery process comprising a step of subjecting the bottom liquor of a rectification tower for acrylic acid to a decomposition evaporation, and a step of subjecting the evaporation residue having a composition of 1–25 wt % of acrylic acid, 9–49% of acrylic acid dimer (the total amount of the acrylic acid and the dimer being in the range of 10–50 wt %) and correspondingly 90–50 wt % of the other components to an extraction with water to separate the acrylic acid, acrylic acid dimer and hydroquinone by the extraction.

The process of the present invention is applicable to any of the usual processes for producing acrylic acid. The usual processes for producing acrylic acid comprises the steps of contacting, with water in the presence of hydroquinone serving as a polymerization inhibitor, an acrylic acid-containing reaction product gas which has been obtained by the catalytic vapor phase oxidation of an olefinic compound represented by a general formula, $CH_2=CHX$, wherein X is at least one member selected from the group consisting of $CH_3$ and CHO, such as propylene and acrolein with a molecular oxygen-containing gas such as air, thereby collecting the acrylic acid in the form of an aqueous solution, and separating the acrylic acid from the aqueous solution. The separation of acrylic acid generally includes the step of removing water from the aqueous solution by extraction with an extraction solvent such as ethyl acetate, ethyl acrylate or the like, the step of separating the solvent, the step of separating by-produced acetic acid from the system, and the step of rectifying the acrylic acid. In certain cases, the extraction step and the solvent separation step may be omitted depending on the collecting conditions of acrylic acid employed in the acrylic acid-collecting step. In this case, only the acrylic acid-rectifying step (conducted by a distillation process or azeotropic distillation process using a required number of distillation towers) is used for the separation of acrylic acid.

The acrylic acid dimer will be produced even in the step of collecting, as an aqueous solution, the acrylic acid formed by the oxidation reaction, and extracted together with acrylic acid in the subsequent extraction operation, with the dimer being increased in amount whenever the distillation operations are undergone. The dimer is fed, as it is, to a final step rectification tower and eventually accumulated in the bottom of the rectification tower. Accordingly, the bottom liquor of the acrylic acid rectification tower contains acrylic acid, acrylic acid dimer, polymerization inhibitor and other high boiling substances. The composition of the bottom liquor may greatly vary depending on the operating conditions of the respective steps but is generally composed of 20–65 wt % of acrylic acid dimer, 5–15 wt % of a polymerization inhibitor such as hydroquinone, and below 20 wt % of high boiling substances.

According to the process of the invention, the bottom liquor is first subjected to an evaporation in such a manner as not only to decompose the acrylic acid dimer contained in the liquor into acrylic acid so as to allow its evaporation together with acrylic acid originally contained in the bottom liquor for recovery as a distillate, but also to distill off part of the acrylic acid dimer. To a surprise, it has been found that this dimer serves as an entrainer and enables the hydroquinone used as a polymerization inhibitor and concentrated in large amount to be simultaneously recovered. The residue in the evaporation step is then subjected to an extraction, with water, of acrylic acid, acrylic acid dimer and hydroquinone while the high boiling substances such as polymeric materials are separated outside the system as a waste oil. In the case, it is necessary that the composition of the residue to be fed to the extraction step using water be composed of 1–25 wt % of acrylic acid, 9–49 wt % of acrylic acid dimer (the total amount of the acrylic acid and the acrylic acid dimer being in the range of 10–50 wt %), and correspondingly 90–50 wt % of other matters such as high boiling substances and hydroquinone. If the composition is outside the upper limit, the high boiling substances are not separable as an oil layer and are suspended in water, so that the separation and recovery of the acrylic acid, its dimer and hydroquinone is made difficult. In case where the evaporation residue is fed to the extraction step with water as it is, it is necessary to control the residue so as to have the above composition. Similarly, when the evaporation residue is further treated as will be described hereinafter, the feed to the water extraction step after the treatment should be controlled to have such composition as indicated above.

The acrylic acid, acrylic acid dimer and hydroquinone which have been collected as a distillate in the above evaporation step can be circulated to a step of separating the acrylic acid from the aqueous solution, with the result that the separated hydroquinone is reusable as a polymerization inhibitor and the acrylic acid contributes to improve the recovery thereof. The separation step in which the above distillate is to be circulated may be any of a solvent extraction step, a solvent separation step, an acetic acid separation step, an acrylic acid refining step and the like step. Of these, the acetic acid separation step is most desirable.

The evaporation residue may be subjected, if necessary, to decomposing and then circulated to the evaporation step. By the circulation, high boiling matters are being accumulated in the system, so that part of the decomposed product is taken out and fed to the water extraction step. Alternatively, part of the decomposed product may be subjected to a further evaporation to recover, as a distillate, acrylic acid, acrylic acid dimer and hydroquinone, followed by circulating to the acrylic acid separation step, e.g. an acrylic acid-refining step, similarly to the case of the afore-discussed evaporation step. The residue to this further evaporation is subjected, if necessary, to decomposing and circulated to the evaporation step, part of which is fed to the water extraction step.

As will be understood from the foregoing, the acrylic acid dimer formed in the system is decomposed into acrylic acid in the evaporation and decomposing steps. The thus decomposed acrylic acid is evaporated and recovered together with acrylic acid dimer and hydroquinone and is reused by recycling to the refining system as an acrylic acid dimer solution with acrylic acid and hydroquinone. Further, non-recovered acrylic acid, acrylic acid dimer and hydroquinone are recovered in the water extraction step as an extract and circulated, as an aqueous solution, for reuse in the above-described steps such as, for example, the acrylic acid-collecting step or the solvent extraction step, preferably the collecting step. Thus, 80–98% of the acrylic acid dimer by-produced in the process of the invention can be recovered as acrylic acid and 70–95% of hydroquinone as a polymerization inhibitor can be collected and reused, ensuring an increase of the refining yield of acrylic acid to a considerable extent and a lowering of the cost of hydroquinone, an expensive polymerization inhibitor, to a great extent.

Figure 2:
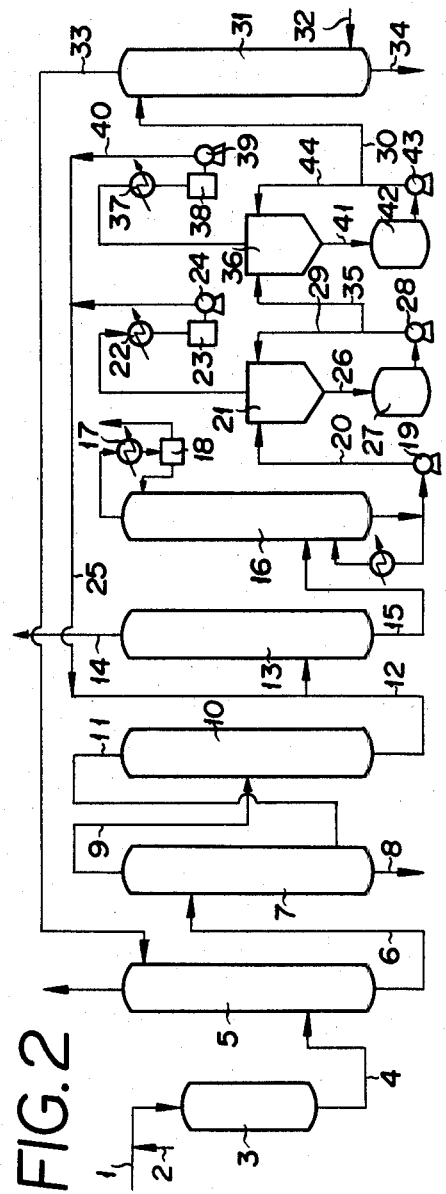

FIG. 1 is a flow sheet showing one embodiment of a process of recovering acrylic acid according to the invention; and FIG. 2 is a flow sheet showing another embodiment according to the process of the invention.

In the system shown in FIG. 1, propylene or acrolein or a mixture thereof fed from a line 1 is catalytically vapor phase oxidized with a molecular oxygen-containing gas such as air fed from a line 2 in a reactor 3. The oxidation reaction product gas containing acrylic acid is fed from a line 4 to an absorption tower 5 in which it is countercurrently contacted with water in the presence of hydroquinone as a polymerization inhibitor to recover acrylic acid as an aqueous solution. The thus obtained aqueous solution containing acrylic acid is fed from a line 6 to an extraction tower 7 in which the aqueous solution is subjected to an extraction with an organic solvent such as ethyl acetate, ethyl acrylate or the like, the water being discharged from a line 8 while the extract being fed from a line 9 to a solvent separation tower 10. The solvent separated in the separation tower 10 is circulated from a line 11 to the extraction tower 7. The acrylic acid and other components are passed from a line 12 into an acetic acid separation tower 13 in which the acetic acid to be a by-product of the oxidation is separated from a line 14 and crude acrylic acid is fed from a line 15 to an acrylic acid rectification tower 16. The acrylic acid is distilled off from the top of the rectification tower 16 and stored through a condenser 17 in a reservoir 18. Though part of the stored acrylic acid is fed back to the rectification tower as a reflux, the remaining is withdrawn as a product. In the bottom of the rectification tower 16 is accumulated acrylic acid which contains, aside from acrylic acid, concentrated acrylic acid dimer, polymerization inhibitors such as hydroquinone, and other high boiling substances such as polymeric materials. This bottom liquor is fed, by means of a pump 19, to an acrylic acid dimer decomposition evaporator 21 through a line 20 and the evaporated matter is liquefied in a condenser 22 and stored in a reservoir 23, followed by circulating through a line 25 to an acrylic acid separation step, e.g. to the acetic acid separation tower 13, by means of a pump 24 to recover acrylic acid, acrylic acid dimer and hydroquinone. The stored liquid may be circulated to the solvent extraction tower 7, solvent separation tower 10 or acrylic acid rectification tower 16.

On the other hand, the liquor withdrawn from the bottom is passed through a line 26 and stored in a decomposition vessel 27, part of which is recycled through a pump 28 and a line 29 to the decomposition evaporator 21 for evaporating and recovering the acrylic acid decomposed in the decomposition vessel 27. Another part of the stored liquor is fed through a line 30 to an extraction tower 31. The decomposition evaporator 21 may be of any type and is preferred to be a thin film evaporator. The thin film evaporator is provided with a jacket and has thus such a construction capable of being heated on the heat-transmitting surface such as by steam. Further, the evaporator is required to be used in an operation under reduced pressure so as to ensure separation of acrylic acid from the acrylic acid dimer, hydroquinone as a polymerization inhibitor and other high boiling substances such as polymeric materials. The operating conditions of the decomposition evaporator 21 such as the heating temperature and pressure are generally as follows: a heating temperature ranges 120°–220° C. and the operating pressure ranges 20–500 mmHg.

When polymerization inhibitors such as amine compounds, and organic and inorganic copper compounds are used in combination with hydroquinone in the separating and refining process of acrylic acid, these compounds serve as a decomposition catalyst for converting the acrylic acid dimer into acrylic acid to ensure favorable decomposition of the acrylic acid dimer, thus making it possible to lower the heating temperature at 120°–180° C.

Though the composition of the bottom liquor of the rectification tower which is fed from the line 20 to the decomposition evaporator 21 may greatly vary depending on the operating conditions of the respective steps as described hereinbefore, it generally contains 20–65 wt % of acrylic acid, 30–60 wt % of acrylic acid dimer, 5–15 wt % of hydroquinone polymerization inhibitor, and below 20 wt % of other high boiling substances composed of major proportion of high polymerized materials of acrylic acid. This feed liquor is decomposed and evaporated to a level of 40–80 wt %, condensed in the condenser 22, and, after the condensation, distilled off in the reservoir 23. The distillate has a composition of 20–99 wt % of acrylic acid, 1–60 wt % of acrylic acid dimer, and 0.1–10 wt % of the polymerization inhibitor. On the other hand, the liquor fed through the line 26 to the cracking reservoir 27 has such a composition of 0.5–25 wt % of acrylic acid, 9.5–65 wt % of acrylic acid dimer 5–30 wt % of hydroquinone, and 85–25 wt % of other high boiling substances such as polymeric materials.

Since the acrylic acid dimer is decomposed in the decomposition vessel 27, the vessel has such a construction capable of heating and keeping at a temperature of 120°–220° C., preferably 150°–200° C. and a capacity of 1–8 hours, preferably 3–8 hours, as expressed in terms of a liquor residence time.

The decomposition reaction of the acrylic acid dimer into acrylic acid is assumed to have an equilibrium relation. In practice, the other high boiling substances contain a trimer, tetramer and the like oligomers of acrylic acid and thus the equilibrium relation is established in the multi-components system. Though the decomposition velocity and equilibrium concentration are not known, we have found that no decomposition reaction takes place at temperatures below 120° C. but there occurs dimerization to give an acrylic acid dimer and that the acrylic acid dimer (and trimer, tetramer) is decomposed at above 120° C. In the sense, the decomposition evaporator 21 and decomposition vessel 27 should have heating temperatures above 120° C. The decomposition evaporator 21 is so controlled in temperature and pressure within the above-defined ranges as to evaporate acrylic acid and part of acrylic acid dimer but not to evaporate the other high boiling substances such as highly polymerized materials except for the dimer. In the so-controlled evaporator 21, the acrylic acid dimer acts as an entrainer for the hydroquinone upon the distillation, making it possible to collect the hydroquinone as an acrylic acid dimer solution.

In the decomposition evaporator 21, the acrylic acid is immediately distilled off outside the system after the decomposition reaction, so that the equilibrium varies to favor formation of acrylic acid, making the decomposition reaction to proceed smoothly. Thus, it will suffice that the residence time is as low as about 10 minutes. However, the acrylic acid decomposed in the decomposition vessel 27 is not discharged outside the system, so that the residence time of 1-8 hours is necessary as indicated above. Though a necessary residence time varies depending on the heating temperature and the composition of the liquor, a residence time 3-8 hours is required in consideration of the conditions of the temperature and composition in decomposition vessel 27. The residence time more than 10 hours does not show any merit on the decomposition from a standpoint of the equilibrium relation, thus being disadvantageous economically.

In case of feeding a part of the outlet liquor from the decomposition vessel 27 to the extraction tower 31, when the total content of acrylic acid and its dimer in the liquor composition withdrawn from the decomposition vessel 27 exceeds 50 wt % due to the lack of either the decomposition of the acrylic acid dimer in the decomposition evaporator 21 and decomposition vessel 27 or the distilling of the acrylic acid or its dimer from the above apparatus, the liquor exhibits such a nature as to form a homogeneous phase in cooperation with water in the extraction tower, rendering the extraction impossible. On the other hand, when the decomposition of the acrylic acid dimer is made to proceed excessively and the acrylic acid and its dimer are recovered outside the system so that the total amount of acrylic acid and its dimer in the liquor composition is not greater than 10 wt %, the liquor is turned solid at a normal temperature and becomes impossible to extract. Accordingly, in order to feed the outlet liquor from the decomposition vessel 27 to the extraction tower 31, the total amount of acrylic acid and its dimer in the liquor composition must be controlled to be in the range of below 50 wt %, generally 20-45 wt %, in consideration of the liquor composition fed from the decomposition evaporator 21 and by suitably selecting the afore-indicated operating conditions.

The solution of acrylic acid, dimer and hydroquinone which is a distillate from the decomposition evaporator 21 is circulated to the solvent separation step and the acetic acid separation step and then recovered for reuse as a polymerization inhibitor.

The liquor of the decomposition vessel 27 withdrawn from the decomposition evaporation 21 is fed through a pump 28 and a line 30 to the upper portion of an extraction tower 31, while water is fed from the lower portion of the extraction tower through a line 32 to effect the countercurrent extraction. The extract is recovered through a line 33 in the form of an aqueous solution of acrylic acid, its dimer and hydroquinone, and is fed, as it is, to a step of collecting the acrylic acid in an aqueous form (absorption tower 5) and any steps between the acrylic acid extraction step and the solvent separation step for use as a polymerization inhibitor. On the other hand, the other high boiling substances such as polymeric materials are withdrawn through a line 34 to outside and treated as a waste oil.

The extraction tower 31 may be of any type. Preferably, a rotary disc-type extraction tower is used since the extraction residue is highly viscous and sticky.

The extracting conditions include a temperature of 5°-90° C., preferably 20°-60° C., and a extracting reagent ratio, i.e. the liquor withdrawn from the bottom: water = 1:1-10 (W/W), preferably 1:3-6. The recoveries of the acrylic acid dimer and hydroquinone in the extraction tower are found to be in the ranges of 70-95 wt % and 50-90 wt %, respectively. Even if the water is used in larger amount so that the extracting reagent ratio is in the range of 1:6 or more, the recovery of the acrylic acid dimer or hydroquinone does not increase but such use is rather disadvantageous in economy since the dimer or hydroquinone has to be recovered as a more diluted aqueous solution. When, on the other hand, the extracting reagent ratio of 1:3 or less is used to reduce the amount of water, the recovery of the acrylic acid dimer is abruptly lowered, with the hydroquinone being lowered in recovery. If the ratio is in the range of 1:1 or smaller, a homogeneous phase is formed and thus the extraction becomes impossible.

FIG. 2 shows another embodiment according to the invention, in which the liquor withdrawn from the first decomposition evaporator 21 is fed through a line 26 to the decomposition vessel 27. Part of the liquor is recycled to the decomposition evaporator 21 through a line 35 and a second evaporator 36. The evaporated matter is liquefied in a condenser 37 and stored in a reservoir 38, and recovered for reuse as an acrylic acid dimer solution of acrylic acid and hydroquinone by feeding to the above-indicated steps through a pump 39 and a line 40. While, the liquor withdrawn from the bottom of the evaporator 36 is stored in a decomposition vessel 42 through a line 41, part of which is recycled to the evaporator 36 through a pump 43 and a line 44, another part is passed through the line 30 to the extraction tower 31. Though the decomposition evaporator 36 may be of any type, the same type as of the first decomposition evaporator 21 is ordinarily employed. The operating conditions of the second evaporator are similar to those of the first decomposition evaporator 21.

It will be noted that since the embodiment of FIG. 2 is the same as that of FIG. 1 except that such arrangement as specifically described above is used, like reference numerals in FIGS. 1 and 2 show like parts or apparatus.

As will be clear from the foregoing, it is essential to add a polymerization inhibitor such as hydroquinone to the separating and refining step for acrylic acid. Though it is impossible to completely suppress formation of the acrylic acid dimer, the process according to the invention using the acrylic acid dimer decomposition evaporators 21 and 36, the decomposition vessels 27 and 42 and the extractor can realize a recovery of the added hydroquinone at 70-95% and a recovery of acrylic acid by decomposing 80-98 wt % of the formed acrylic acid dimer. Simultaneously, the acrylic acid contained in the bottom liquor of the rectification tower can be recovered at 90 wt % or more, increasing the refining yield to a remarkable extent.

If the extraction tower is not used in the process of the invention, there can be recovered an acrylic acid dimer solution of hydroquinone, not an aqueous solution containing acrylic acid dimer and hydroquinone. In the case, however, the recovery of the acrylic acid dimer or hydroquinone will be inevitably lowered.

An important aspect of the invention is that acrylic acid and its dimer are decomposed and evaporated as much as possible while recovering hydroquinone at the same time, without evaporating the high boiling substances such as polymeric materials, by either increasing the heating temperature or reducing the operating pressure in the decomposition evaporation step.

As a matter of course, the total amount of acrylic acid and its dimer in the liquor composition withdrawn from the bottom of the evaporator 21 or 36 will ultimately decrease to a level of below 10 wt % and such liquor can not be thus subjected to extraction, being suitably discharged as a waste oil.

The recovering effect according to the invention will be particularly illustrated by way of examples.

EXAMPLE I

There was provided an acrylic acid production apparatus which had an annual capacity of production of 25,000 tons and which was adapted to carry out the catalytic vapor phase oxidation process using propylene as a starting material and hydroquinone as a polymerization inhibitor. The apparatus was provided with an acrylic acid dimer decomposition evaporation apparatus of the thin film evaporator type having a heat transmitting area of 3.0 m² and including a decomposition vessel with a capacity of 1 m³ and further with a 20-stage rotary disc-type extraction tower with an inner diameter of 400 mm.

The decomposition evaporation apparatus was so arranged as to be heated by means of steam of 180° C. and the pressure in the system was reduced to 50 mmHg. The decomposition reservoir was heated to 180° C. Under these operating conditions, the bottom liquor from a rectification tower of the acrylic acid production apparatus was fed to the decomposition evaporation apparatus. As a result, it was found that the amount of evaporation of the liquor reached 76.0 wt %. The feed liquor, distillate, and liquor withdrawn from the bottom of the decomposition evaporation apparatus and outlet liquor from the decomposition vessel had such compositions as shown in Table 1, respectively. The rate of decomposition of the acrylic acid dimer into acrylic acid and the recovery of hydroquinone in the decomposition evaporation apparatus and decomposition vessel were found to be 48.9% (97.8% based on the produced dimer) and 36.9%, respectively.

After the decomposition and evaporation, the liquor withdrawn from the apparatus was fed to the upper portion of the extraction tower while feeding water in an amount five times (W/W) as great as that of the feed liquor from the lower portion of the extraction tower at a normal temperature thereby extracting the acrylic acid dimer and hydroquinone countercurrently. As a consequence, an aqueous solution containing the acrylic acid dimer and hydroquinone in amounts of 5 wt % and 2 wt %, respectively, was recovered from the upper portion of the extraction tower. The recoveries were found to be 90% for acrylic acid dimer and 80% for hydroquinone. About 50% of the oily residue based on the feed liquor was withdrawn from the lower portion of the extraction tower and discharged as a waste oil. The total recovery rates of acrylic acid dimer and hydroquinone were 94.9 wt % and 87.4 wt % respectively. The acrylic acid and the acrylic acid dimer solution of hyroquinone recovered from the decomposition evaporation apparatus were fed to a solvent separation step and an acetic acid separation step of the acrylic acid production apparatus, and the aqueous solution of the acrylic acid dimer and hydroquinone recovered from the extraction tower was passed through an acrylic acid-collecting step and an acrylic acid-extracting step to the solvent separation step for reuse as a polymerization inhibitor. Six months or more after commencement of the operation, the acrylic acid production apparatus could be favorably operated without involving any troubles such as concentration or deposition of high boiling substances such as polymeric materials in the above-indicated steps. During the operation, the cost of hydroquinone was reduced to 1/5 times that required by processes using no recovery process of the present invention and the refining yield of acrylic acid was increased by about 3%.

TABLE 1

| | (unit: wt %) | | | |
|---|---|---|---|---|
| | acrylic acid | acrylic acid dimer | hydro-quinone | other high boiling substances |
| feed liquor | 36.1 | 48.1 | 6.5 | 9.3 |
| distillate | 77.8 | 18.1 | 3.1 | 1.0 |
| liquor withdrawn from bottom | 2.1 | 40.8 | 17.1 | 40.0 |
| outlet liquor from the decomposition vessel | 11.6 | 30.3 | 17.1 | 41.0 |

EXAMPLE II

The same apparatus and operating conditions as in Example I were used except that the extraction was conducted under such extracting conditions (extracting reagent ratio) that water was used in an amount of two times (W/W) as great as that of the feed liquor. As a result, it was found that the recoveries of the acrylic acid dimer and hydroquinone at the extraction tower were 60.1 wt % and 70.3 wt %, respectively.

EXAMPLE III

The same apparatus and conditions as in Example I were used except that hydroquinone and a copper diethyldithiocarbamate (0.1 wt %, as copper, in the feed liquor from the dimer decomposition evaporation apparatus) were used as polymerization inhibitor. The decomposing and recovering effect similar to the case of Example 1 was obtained at a decomposition temperature of 160° C. by the catalytic action of the copper compound.

EXAMPLE IV

When the same apparatus and conditions as in Example I were used except that the acrylic acid dimer decomposition evaporation apparatus was operated under conditions of a heating temperature of 180° C. and a pressure of 20 mmHg, 85% of the feed liquor was distilled. Feed liquor distillate, and liquor withdrawn from the bottom and outlet liquor from the decomposition vessel are shown in Table II below.

In the decomposition evaporation apparatus, the decomposition recovery of the acrylic acid dimer was found to be 36.6% (97% based on the amount of production in the system) and the recovery of hydroquinone was 49.2%. The total recovery rates of acrylic acid dimer and hydroquinone were 84.1 wt % respectively.

TABLE II

| | (unit: wt %) | | | |
|---|---|---|---|---|
| | acrylic acid | acrylic acid dimer | hydro-quinone | other high boiling matters |
| feed liquor | 36.1 | 48.1 | 6.5 | 9.3 |
| distillate | 62.9 | 26.2 | 3.8 | 7.1 |
| liquor withdrawn from bottom | 1.1 | 26.9 | 22.0 | 50.0 |
| outlet liquor from the decomposition vessel | 10.5 | 17.5 | 22.0 | 50.0 |

COMPARATIVE EXAMPLE I

When the same apparatus and conditions as in Example I were used except that the bottom liquor from the rectification tower of the acrylic acid production apparatus was directly fed into the extraction tower without passing through the decomposition evaporation apparatus, a homogeneous phase was formed and thus the extraction could not be conducted, with the acrylic acid dimer and hydroquinone not being recoverable.

COMPARATIVE EXAMPLE II

When the same apparatus and conditions as in Example I were used except that the extraction was effected under such extraction conditions (extracting reagent ratio) that water was used in an amount of 0.6 times (W/W) as small as that of the feed liquor, a homogeneous phase was formed in the tower, making it impossible to extract. Neither acrylic acid dimer nor hydroquinone could be recovered in the extracting process.

EXAMPLE V

The apparatus was provided with two acrylic acid dimer decomposition evaporation apparatus of the same type used in Example I in series and further with a 20-stage rotary disc-type extraction tower with an inner diameter of 400 mm as is shown in FIG. 2.

The two of the decomposition evaporation apparatus were both so arranged as to be heated by means of steam of 180° C., and the pressure in the 1st stage system was reduced to 300 mmHg, and in the 2nd stage system it was reduced to 80 mmHg. Each of the decomposition vessels was heated to 180° C. Under these conditions, the bottom liquor from the rectification tower of the acrylic acid production apparatus as shown in Example 1, was fed to the 1st stage decomposition evaporation apparatus. It was found that the amounts of evaporation of the liquor reached 55.6 wt % the 1st stage and 63.0 wt % in the 2nd stage.

The feed liquors, distillates and liquors withdrawn from the bottoms of the decomposition evaporation apparatus and outlet liquors from the decomposition vessels had such compositions as shown in Table III, respectively. The total rate of decomposition of the acrylic acid dimer into acrylic acid and the recovery of hydroquinone in these decomposition evaporation apparatus and decomposition vessels were found to be 49.2 wt % (96 wt % based on the produced dimer) and 58.3 wt %, respectively.

After the decomposition and evaporation, the liquor withdrawn from the decomposition vessel of the 2nd stage system was fed to the upper portion of the extraction tower while feeding water in an amount five times (W/W) as great as that of the feed liquor from the lower portion of the extraction column at a normal temperature thereby extracting the acrylic acid dimer and hydroquinone countercurrently. As a consequence, an aqueous solution containing the acrylic acid dimer and hydroquinone in amounts of 5 wt % and 2 wt %, respectively, was recovered from the upper portion of the extraction tower. The recoveries were found to be 75 wt % for acrylic acid dimer and 80 wt % for hydroquinone. About 50% of the oil residue based on the feed liquor was withdrawn from the lower portion of the extraction tower and discharged as a waste oil. Total recovery rates of acrylic acid dimer and hydroquinone were 87.3% and 91.7% respectively. The acrylic acid and the acrylic acid dimer solution of hydroquinone recovered from the decomposition evaporation apparatus were fed to a solvent separation step and an acetic acid separation step of the acrylic acid production apparatus, and the aqueous solution of the acrylic acid dimer and hydroquinone recovered from the extraction tower was passed through an acrylic acid-collecting step and an acrylic acid-extracting step to the solvent separation step for reuse as a polymerization inhibitor.

TABLE III (unit: wt %)

| | | acrylic acid | acrylic acid dimer | hydroquinone | other high boiling substances |
|---|---|---|---|---|---|
| feed liquors | 1st stage | 39.1 | 44.9 | 6.5 | 9.5 |
| | 2nd stage | 13.0 | 47.3 | 14.0 | 25.7 |
| distillates | 1st stage | 97.0 | 2.0 | 0.5 | 0.5 |
| | 2nd stage | 25.3 | 55.4 | 11.4 | 7.9 |
| liquors withdrawn from the bottom | 1st stage | 3.1 | 57.6 | 14.0 | 25.3 |
| | 2nd stage | 1.0 | 25.2 | 18.3 | 55.5 |
| outlet liquors from the decomposition vessel | 1st stage | 13.0 | 47.3 | 14.0 | 25.7 |
| | 2nd stage | 9.2 | 16.4 | 18.3 | 56.1 |

COMPARATIVE EXAMPLE III

When the same apparatus and conditions as in Example V were used except that the 2nd stage acrylic acid dimer decomposition evaporation apparatus was operated under conditions of a heating temperature of 180° C. and a pressure of 10 mmHg, 85% of the feed liquor was distilled off. The feed liquor, distillates, liquor withdrawn from the bottom and outlet liquors from decomposition vessels are shown in Table IV.

The liquor withdrawn from the 2nd stage decomposition vessel was turned solid at a normal temperature, from which neither acrylic acid dimer nor hydroquinone could be recovered in the extraction tower. In the decomposition evaporation apparatus, the rates of recovery of the acrylic acid dimer and hydroquinone were 54.1% and 70.8%, respectively.

TABLE IV (unit: wt %)

| | | acrylic acid | acrylic acid dimer | hydroquinone | other high boiling substances |
|---|---|---|---|---|---|
| feed liquors | 1st stage | 39.1 | 44.9 | 6.5 | 9.5 |
| | 2nd stage | 13.0 | 47.3 | 14.0 | 25.7 |
| distillates | 1st stage | 97.0 | 2.0 | 0.5 | 0.5 |
| | 2nd stage | 20.0 | 64.6 | 9.1 | 6.3 |
| liquors withdrawn from the bottom | 1st stage | 3.1 | 57.6 | 14.0 | 25.3 |
| | 2nd stage | 0.2 | 7.5 | 22.9 | 69.9 |
| outlet liquors from the decomposition vessel | 1st stage | 13.0 | 47.3 | 14.0 | 25.7 |
| | 2nd stage | 3.5 | 6.0 | 22.9 | 67.6 |

What is claimed is:
1. A process for preparing acrylic acid comprising:
   (a) catalytic vapor phase oxidation of an olefinic compound of the general formula $CH_2=CHX$ wherein X represents at least one group selected from the group consisting of $CH_3$ and CHO with a molecu- lar oxygen containing gas to yield a reaction product gas comprising acrylic acid and acetic acid, (b) contacting said reaction product gas with water in the presence of hydroquinone and obtaining an aqueous solution of said reaction product and hydroquinone, (c) separating the acrylic acid from the aqueous solution, which comprises the steps of
  (i) separating the organic components containing said reaction product and hydroquinone from the aqueous solution by extraction.
  (ii) separating acetic acid from the organic components to obtain the crude acrylic acid by distillation, and
  (iii) separating the acrylic acid from the crude acrylic acid and obtaining a bottom liquor containing acrylic acid, acrylic acid dimer, hydroquinone and high boiling substances by distillation, (d) decomposition evaporating said bottom liquor under reduced pressure of 20-500 mmHg at a temperature of 120°-220° C. to provide a distillate and an evaporation residue having the composition of 1-25 wt % of acrylic acid, 9-49 wt % of acrylic acid dimer, wherein the total amount of the acrylic acid and its dimer is in the range of 10-50 wt % and correspondingly 90-50 wt % of the other components, said distillate being recycled to step c, and (e) subjecting said evaporation residue to water extraction to separate said acrylic acid, acrylic acid dimer, and hydroquinone as aqueous solution from high boiling water insoluble substances, said aqueous solution being recycled to the step b or step c-i.

2. A process according to claim 1, wherein the distillate obtained by the decomposition evaporation of the bottom liquor from the step d is circulated to the acetic acid separation step c-ii.

3. A process according to claim 1, wherein the decomposition of the evaporation residue is conducted at 150°-200° C.

4. A process according to claim 1 wherein the acrylic acid, acrylic acid dimer and hydroquinone recovered as an aqueous solution by the water extraction are circulated to the step b.

5. A process according to claim 1, wherein the acrylic acid, acrylic acid dimer and hydroquinone recovered as an aqueous solution by the water extraction are circulated to the step c-i.

6. A process according to claim 1, wherein the water extraction is conducted at a temperature of 5°-90° C. and at a ratio by weight of the liquor withdrawn from the bottom to water of 1:3-6.

7. A process according to claim 6, wherein the water extraction is conducted at a temperature of 20°-60° C. and a ratio by weight of the liquor withdrawn from the bottom to water of 1:3-6.

8. A process according to claim 1, wherein the evaporation residue is further subjected to decomposition evaporation and the residue after the decomposition is subjected to water extraction.

9. A process according to claim 8, wherein the distillate obtained by the further decomposition evaporation is circulated to the acrylic acid separation step c.

10. A process according to claim 8, wherein the acrylic acid, acrylic acid dimer and hydroquinone recovered as an aqueous solution by the water extraction are circulated to the step b.

* * * * *